(12) United States Patent
Calleri

(10) Patent No.: US 11,441,989 B1
(45) Date of Patent: Sep. 13, 2022

(54) METHOD AND APPARATUS FOR CARRYING OUT RHEOLOGIC MEASUREMENTS OF A DRILLING MUD

(71) Applicant: Geolog S.r.l., Milan (IT)

(72) Inventor: Antonio Calleri, Milan (IT)

(73) Assignee: Geolog S.r.l., San Glullano Milanese (IT)

( * ) Notice: Subject to any disclaimer, the term of this patent is extended or adjusted under 35 U.S.C. 154(b) by 0 days.

(21) Appl. No.: 17/679,157

(22) Filed: Feb. 24, 2020

(30) Foreign Application Priority Data

Feb. 26, 2021 (IT) .................. 102021000004568

(51) Int. Cl.
*H01H 47/00* (2006.01)
*G01N 11/04* (2006.01)
(Continued)

(52) U.S. Cl.
CPC ......... *G01N 11/04* (2013.01); *G01N 33/2823* (2013.01); *H01F 7/20* (2013.01); *H01F 27/28* (2013.01)

(58) Field of Classification Search
None
See application file for complete search history.

(56) References Cited

U.S. PATENT DOCUMENTS

2009/0090172 A1* 4/2009 Angelescu ............ G01N 11/08
702/50
2019/0094119 A1* 3/2019 Singh .................... G01N 11/04

FOREIGN PATENT DOCUMENTS

CN 108827830 11/2018
FR 3094091 9/2020

OTHER PUBLICATIONS

Rapporto di Ricerca e Opinione Scritta [Search Report and Written Opinion] Dated Nov. 17, 2021 From the Ministero Dello Sviluppo Economico, Direzione Generale Sviluppo Produttivo e Competitivita, Ufficio Italiano Brevetti e Marchi Re. Application No. IT202100004568. (9 Pages).

* cited by examiner

*Primary Examiner* — Stephen W Jackson

(57) ABSTRACT

Method for carrying out rheologic measurements of a drilling mud, comprising: providing a first toroidal conduit (10); inserting into said first toroidal conduit (10) a drilling mud, comprising drilling debris; determining conditions to be simulated for said mud, said conditions to be simulated comprising a path length and/or a flow time to be simulated for said mud; determining, as a function of said conditions to be simulated, operating conditions to be applied to said mud, said operating conditions comprising a number of laps around said first toroidal conduit (10) and/or a flow time in said first toroidal conduit (10); regulating the temperature inside said first toroidal conduit (10); regulating the pressure inside said first toroidal conduit (10); providing a displacement device (20) comprising a first projectile (21), wherein said first projectile (21) fills substantially entirely a cross-section of said first toroidal conduit (10); moving, by means of said first projectile (21), said mud in the first annular conduit (10) according to said operating conditions. The method further comprises: a first operating step, wherein a force is determined, which is applied by said displacement device (20) to move said mud in the first toroidal conduit (10); a second operating step, wherein a rheologic parameter of said mud is determined as a function of said force.

21 Claims, 6 Drawing Sheets

(51) Int. Cl.
*G01N 33/28* (2006.01)
*H01F 27/28* (2006.01)
*H01F 7/20* (2006.01)

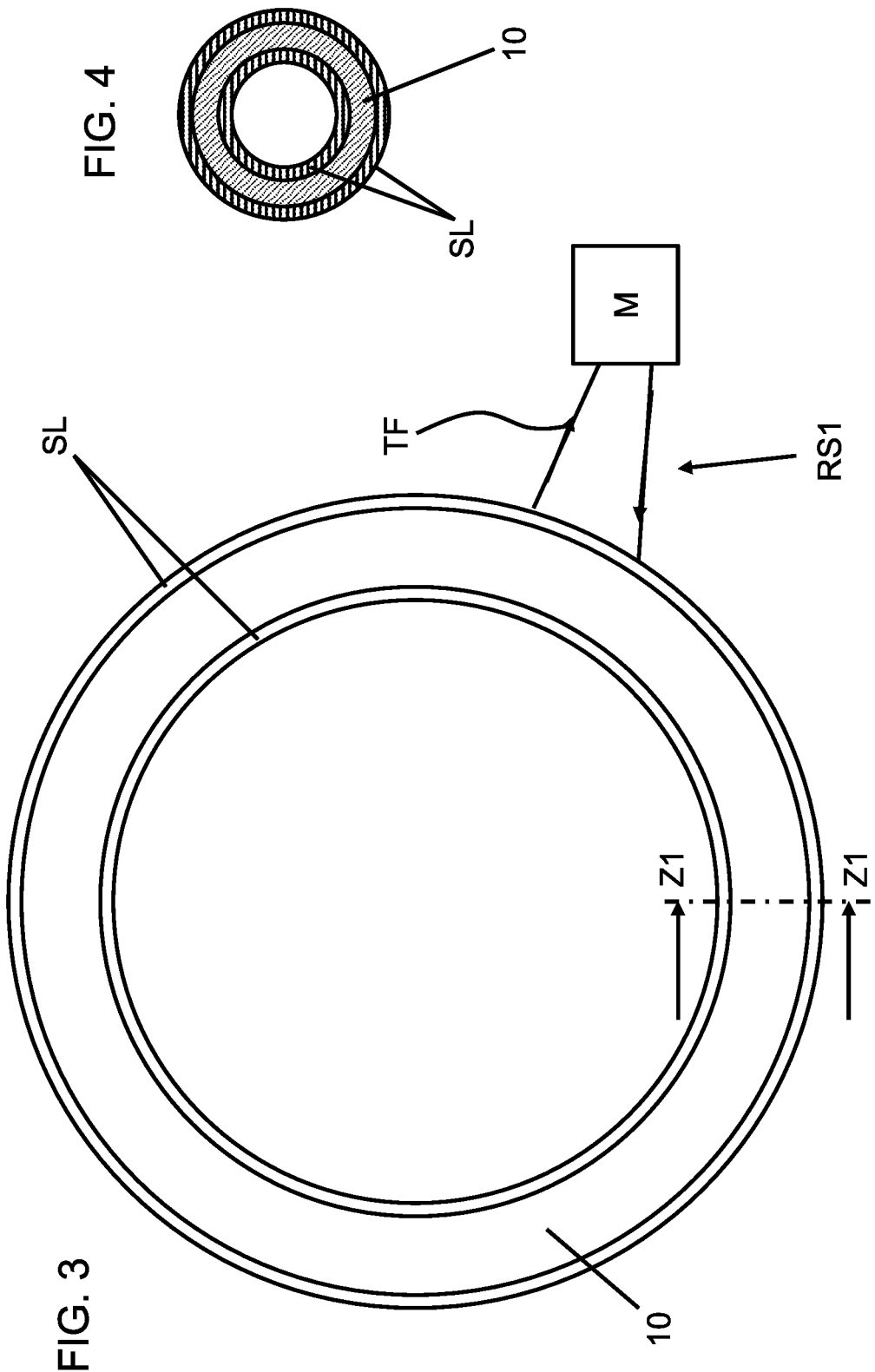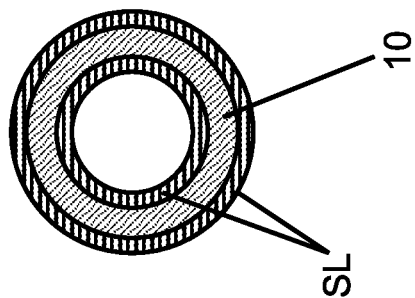

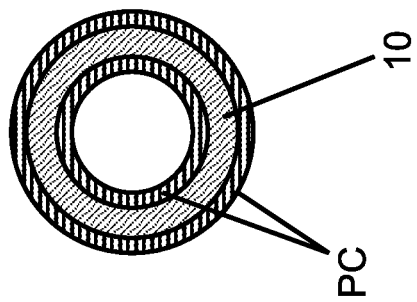
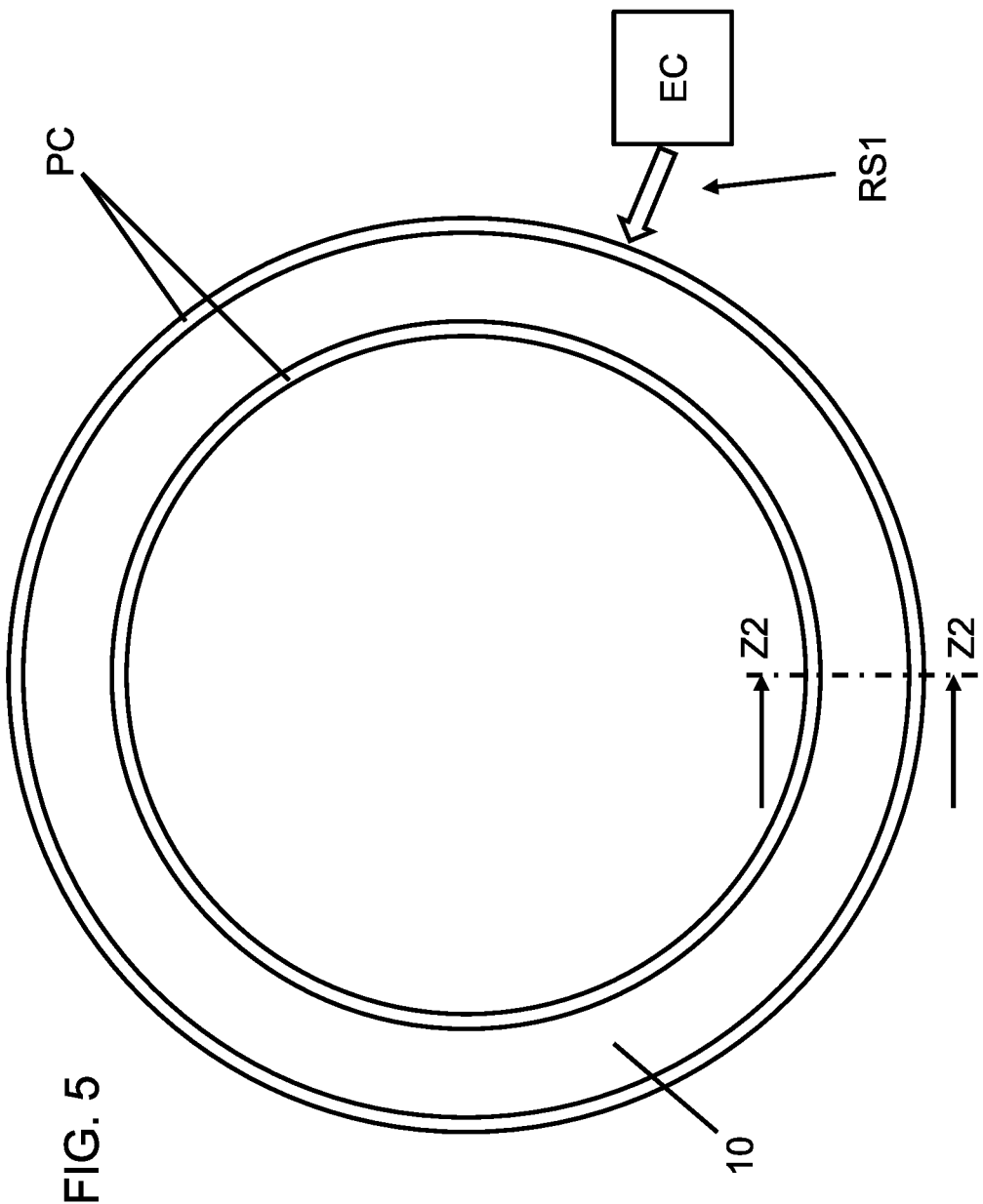

METHOD AND APPARATUS FOR CARRYING OUT RHEOLOGIC MEASUREMENTS OF A DRILLING MUD

RELATED APPLICATION

This application claims the benefit of priority of Italy Patent Application No. 102021000004568 filed on Feb. 26, 2021, the contents of which are incorporated by reference as if fully set forth herein in their entirety.

FIELD AND BACKGROUND OF THE INVENTION

The present invention relates to a method for carrying out rheologic measurements of a drilling mud.

The present invention also relates to an apparatus for carrying out rheologic measurements of a drilling mud.

As is known, in several scientific and industrial fields it is necessary to determine rheologic parameters (e.g. viscosity) of a fluid.

For example, in the oil well drilling field it is useful to determine the viscosity of the drilling mud in order to evaluate its performance and, if necessary, change its composition (or select a different one) for subsequent drilling operations.

Rheometers and viscometers are currently available in the art which, via mechanical interaction with a fluid sample, allow the estimation of rheologic parameters of interest.

The Applicant observed that the physical properties of a drilling mud and its interaction with the outside environment (e.g. a porous medium), with particular reference to rheologic quantities, vary as a function of the conditions in which the mud is operating and the recent "history" of the mud itself, such as, for example, the distance it has covered while flowing, under certain temperature and pressure conditions, in a conduit.

The Applicant also observed that the measurement tools available today do not permit taking into account all those factors which can substantially affect the rheologic parameters of the fluids of interest in the oil&gas industry (drilling, production, etc.), and therefore cannot provide accurate and reliable measurements.

SUMMARY OF THE INVENTION

It is therefore one object of the present invention to provide a method and an apparatus for carrying out rheologic measurements of a drilling mud which can provide accurate and reliable data, and which, in particular, can take into account the dynamic and physical conditions to which the mud has been previously subjected.

This and other objects are substantially achieved by a method and an apparatus as set out in the appended claims.

BRIEF DESCRIPTION OF THE SEVERAL VIEWS OF THE DRAWINGS

Further features and advantages will become more apparent in the light of the following detailed description of a preferred, but non-limiting, embodiment of the invention. Such description is provided herein with reference to the annexed drawings, which are also supplied by way of non-limiting example, wherein:

FIG. 3 schematically shows an embodiment of the apparatus of FIG. 1;

FIG. 4 shows a sectional view of the apparatus of FIG. 5 in the plane defined by line Z1-Z1;

FIG. 5 schematically shows an embodiment of the apparatus of FIG. 1;

FIG. 6 shows a sectional view of the apparatus of FIG. 5 in the plane defined by line Z2-Z2;

DESCRIPTION OF SPECIFIC EMBODIMENTS OF THE INVENTION

Figure 2:
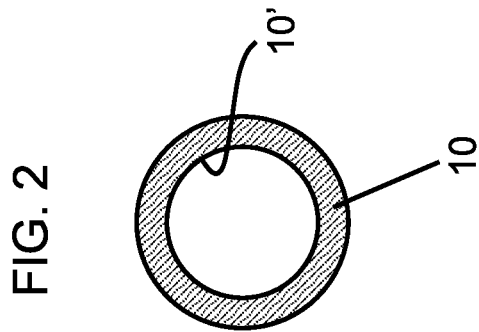
FIG. 2 shows a sectional view of the apparatus of FIG. 1 in the plane defined by line Y-Y.
Figure 1:
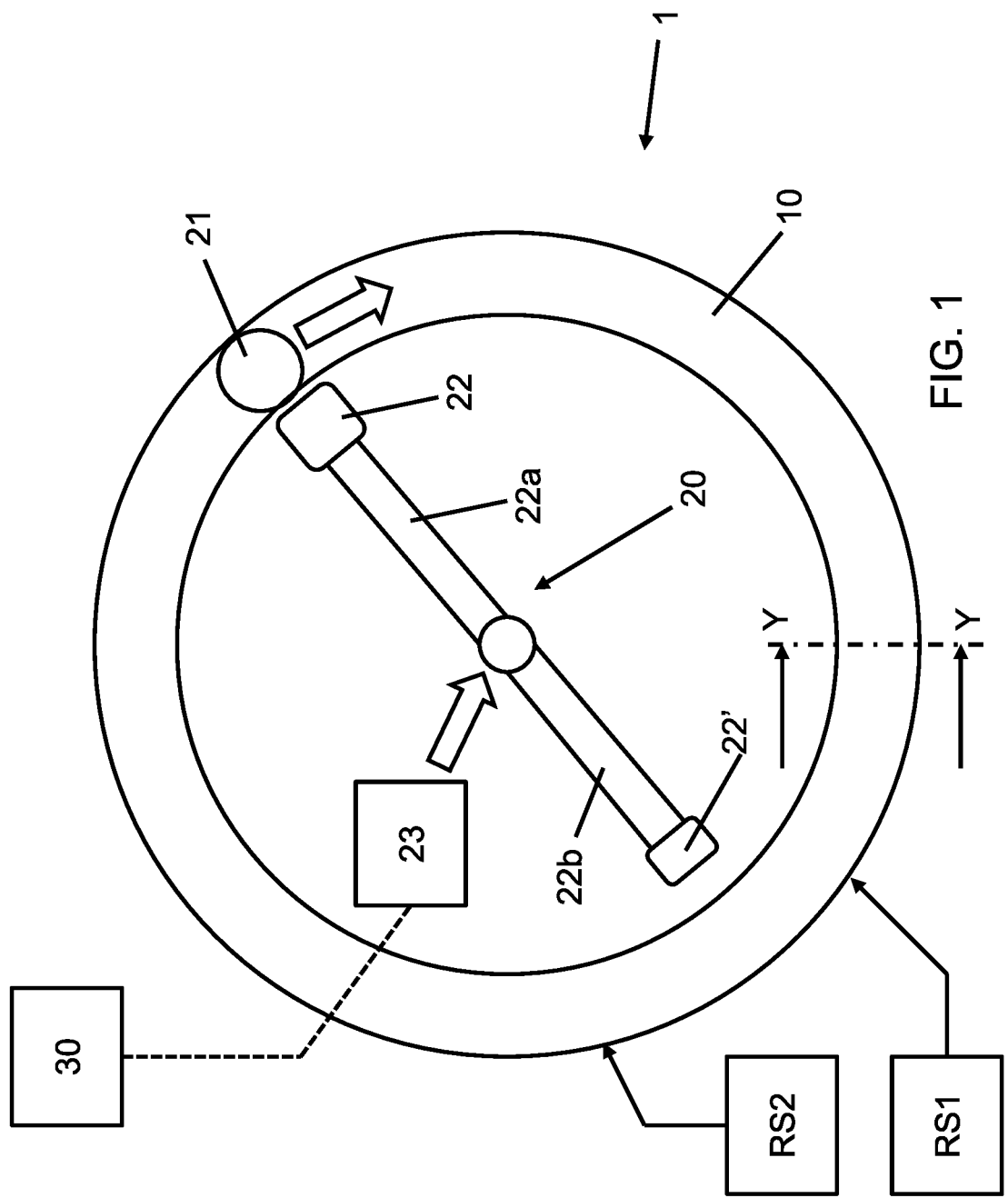
FIG. 1 schematically shows a plan view of an apparatus according to the present invention.

With reference to the annexed drawings, reference numeral 1 designates an apparatus for carrying out rheologic measurements of a drilling mud in accordance with the present invention.

The mud involved in the present invention comprises drilling debris.

In other words, along with a basic fluidic substance, further substances/elements are also introduced into the system, such as rocky fragments typically transported by the mud used in drilling rigs along the path extending from well bottom to ground level.

First and foremost, the apparatus 1 comprises at least one first closed toroidal conduit 10.

For example, the first toroidal conduit 10 has, in a plan view, a substantially circular shape, as schematically shown in FIGS. 1, 3, 5 and 7.

In a cross-sectional view, the first toroidal conduit 10 has, preferably, a substantially circular profile, as schematically shown in FIGS. 2, 4 and 6. Nevertheless, the first toroidal conduit may also have, in a cross-sectional view, a different profile (e.g. oval, elliptical).

Preferably, the first toroidal conduit 10 has an aperture 11 (FIGS. 8a-8b), which can be selectively closed, for inserting drilling mud into the first toroidal conduit 10. The mud in the first toroidal conduit 10 is the mud for which one or more rheologic parameters will be determined.

Preferably, the apparatus 1 comprises a closing element 12a, 12b (FIGS. 8a-8b) coupled to the aperture 11 and drivable between a first condition, in which it sealingly closes the aperture 11, and a condition in which it opens, at least partially, said aperture 11.

Figure 8B:
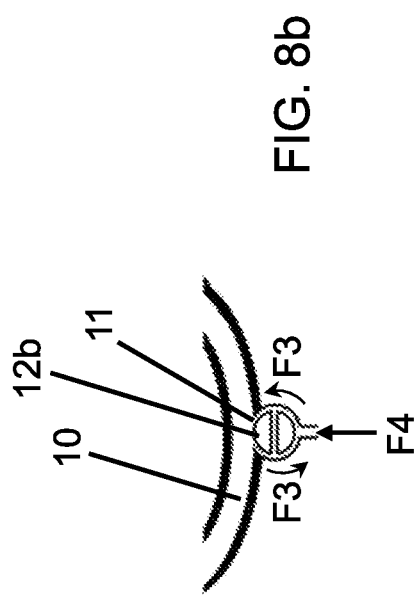
FIGS. 8a-8b schematically show some possible embodiments of a detail of the apparatus of FIG. 1.
Figure 8A:
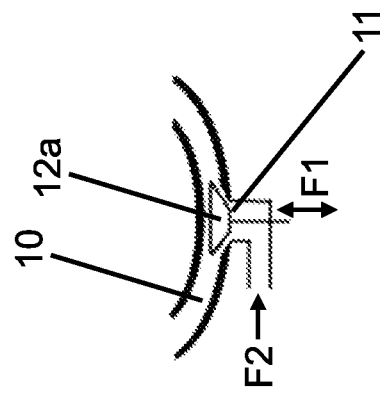

More in detail, the closing element 12a shown in FIG. 8a has a tapered conformation, so that it acts like some sort of plug upon the aperture 11. The closing element 12a can be moved in the directions indicated by arrow F1 (e.g. driven by a suitable servo mechanism, not shown), so as to selectively obstruct the aperture 11. When the closing element 12a is in the opening condition, it allows the mud to be inserted in the direction indicated by arrow F2.

FIG. 8b schematically shows a different closing element 12b. The closing element 12b is designed substantially as a ball provided with a diametrical through hole that, depending on its orientation, selectively closes the aperture 11. In other words, the closing element 12b can rotate (e.g. under the action of a suitable servo mechanism, not shown) as shown by arrows F3. When the through hole is oriented vertically—in the reference system of FIG. 8b—the mud can be inserted in the direction indicated by arrow F4.

The apparatus 1 comprises a first regulation system RS1 for regulating the temperature inside the first toroidal conduit 10.

In one embodiment (FIGS. 3-4), the first regulation system RS1 comprises a sleeve SL externally associated with the first toroidal conduit 10, a thermovector fluid TF, and a regulation module M for regulating the temperature of the thermovector fluid TF. By controlling the temperature of the thermovector fluid TF and having the latter propagate inside the sleeve SL, it is possible to adjust the temperature inside the first toroidal conduit 10.

In one embodiment, the first regulation system RS1 comprises one or more Peltier cells PC externally applied to the first toroidal conduit 10, and an electric circuit EC associated with said one or more Peltier cells PC in order to supply power thereto. By controlling the power supplied to the Peltier cells PC, it is possible to adjust the temperature of the same and hence the temperature inside the first toroidal conduit 10.

By way of example, the temperature inside the first toroidal conduit 10 is in the range of 4° C. to 200° C., preferably 10° C. to 160° C.

The apparatus 1 comprises a second regulation system RS2 for regulating the pressure inside the first toroidal conduit 10.

By way of example, the pressure inside the first toroidal conduit 10 is in the range of 1 bar to 200 bar, preferably 10 bar to 170 bar.

The apparatus 1 comprises a displacement device 20 configured for moving the mud inside the first toroidal conduit 10, so that such mud will flow in the first toroidal conduit 10.

Preferably, the displacement device 20 (FIG. 1) comprises a first projectile 21 housed inside the first toroidal conduit 10.

The first projectile 21 may have, for example, a spherical shape or any other shape allowing it to move inside the first toroidal conduit 10, substantially in contact with (e.g. sliding on) the radially internal surface 10' of the first toroidal conduit 10, so as to prevent the mud contained therein from leaking between said radially internal surface 10' and the external surface of the first projectile 21.

In other words, the first projectile 21 occupies, substantially in its entirety, a cross section of the first toroidal conduit 10.

The first projectile 21 generates some sort of "plug flow" in the drilling mud contained in the first toroidal conduit 10.

Advantageously, the first projectile 21 does not alter the properties of the mud under examination in terms of shear rate history, i.e. the shear stresses to which the mud is subjected while moving inside the first toroidal conduit 10.

Preferably, the displacement device 20 comprises an active element 22, external to the first toroidal conduit 10 and magnetically coupled to the first projectile 21.

Preferably, the first projectile 21 is made of magnetic material.

Preferably, the active element 22 is made of magnetic material.

In one embodiment, both the first projectile 21 and the active element 22 are made of magnetic material.

In one embodiment, the first projectile 21 is dragged from the outside, in particular by the active element 22, by electromagnetic induction.

In one embodiment, the first projectile 21 is made of non-magnetic material.

In one embodiment, the active element 22 is made of non-magnetic material.

The displacement device 20 comprises a main actuator 23 connected to the active element 22 and configured for moving the latter along the first toroidal conduit 10.

The main actuator 23 may be implemented as, for example, an appropriately powered and controlled electric motor.

The connection between the active element 22 and the main actuator 23 may comprise an arm 22a. Located in a position opposite the active element 22, fixed to the end of an additional arm 22b, there is a counterweight 22'.

The apparatus 1 comprises a processing unit 30, associated with the displacement device 20 and configured for executing the following steps:

a first operating step, wherein a force is determined, which is applied by the displacement device 20, and in particular by the main actuator 23, to move the mud in the first toroidal conduit 10 by means of the first projectile 21;

a second operating step, wherein a rheologic parameter of the mud is determined as a function of such force.

Advantageously, the first toroidal conduit 10 and the displacement device 20 are used in order to simulate actual conditions in which the mud operates when used in a drilling rig.

More in detail, conditions to be simulated are determined which comprise a mud path length and/or a mud flow time. The conditions to be simulated correspond, therefore, to a distance travelled by the mud in a drilling well (typically from well bottom to ground level, dragging along drilling debris or cuttings) and/or a flow time in the well.

Depending on the conditions that need to be simulated, specific operating conditions are determined which must then be applied to the drilling mud by means of the first toroidal conduit 10 and the displacement device 20. The operating conditions comprise a number of laps along the first toroidal conduit 10 and/or a flow time in the first toroidal conduit 10.

It is thus possible to accurately reproduce the dynamic conditions in which the mud operates, so that its performance can be evaluated in a reliable manner.

In one implementation example, the flow velocity to be simulated is substantially constant, and therefore the path length to be simulated and the flow time to be simulated are mutually correlated in a substantially linear manner.

For example, it is envisaged that a length to be simulated is determined first, and then the number of laps to run inside the first toroidal conduit 10 is computed accordingly based on the geometry—which is known a priori—of the latter.

In one embodiment, the conditions to be simulated are entered into the processing unit 30 via a suitable user interface; the processing unit 30 will then compute the operating conditions to be applied to the mud.

The mud is then moved, by means of the first projectile 21, in the first toroidal conduit 10 in accordance with the above-described operating conditions.

Preferably, said force applied by the displacement device 20 in order to cause the mud to flow in the first toroidal conduit 10 corresponds to a torque that the displacement device 20 itself, and in particular the main actuator 23, exerts in order to keep the mud flowing at a predetermined velocity.

Preferably, said rheologic parameter is determined as a function of such torque.

Preferably, said rheologic parameter comprises a viscosity of the mud.

Preferably, mud viscosity is a function of quantities such as mud temperature and pressure, and depends on a number of parameters such as the percentage, size and nature of the solid particles suspended in the mud, the motion-induced deformation rate, and the stress exerted by the projectile on the mud.

As an example, the following shows a relationship between torque (applied to the projectile by the displacement device), i.e. the measured parameter, and stress, and hence viscosity, i.e. the calculated parameter, based on said geometry. Torque equals stress multiplied by section (cross-sectional area of the first toroidal conduit) multiplied by lever arm (radius of the first toroidal conduit).

$$M = \tau_y \cdot b \cdot A$$
$$\tau_y = \frac{M}{b \cdot A} \cdot C_D$$
$$\dot{\gamma} = \frac{v}{R}$$
$$\eta = \frac{\tau_y}{\dot{\gamma}}$$

Where M is the torque, $\tau_y$ is the stress, b is the lever arm, A is the cross-sectional area of the first toroidal conduit, $C_D$ is the coefficient of friction (of the mud fluid against the inner walls of the first toroidal conduit), $\dot{\gamma}$ is the mean deformation rate profile, v is the mean velocity profile of the mud in the first toroidal conduit, R is the radius of the cross-section of the first toroidal conduit, η is the mean viscosity profile of the mud under examination.

Alternatively, the first projectile 21 may be made of oriented magnetic material; in this embodiment, the first projectile 21 is moved by the magnetic field induced by a current circulating in a suitably insulated solenoid with continuous or non-continuous coils, arranged around the first toroidal conduit, capable of keeping the mud flowing at a predetermined velocity.

Figure 9:
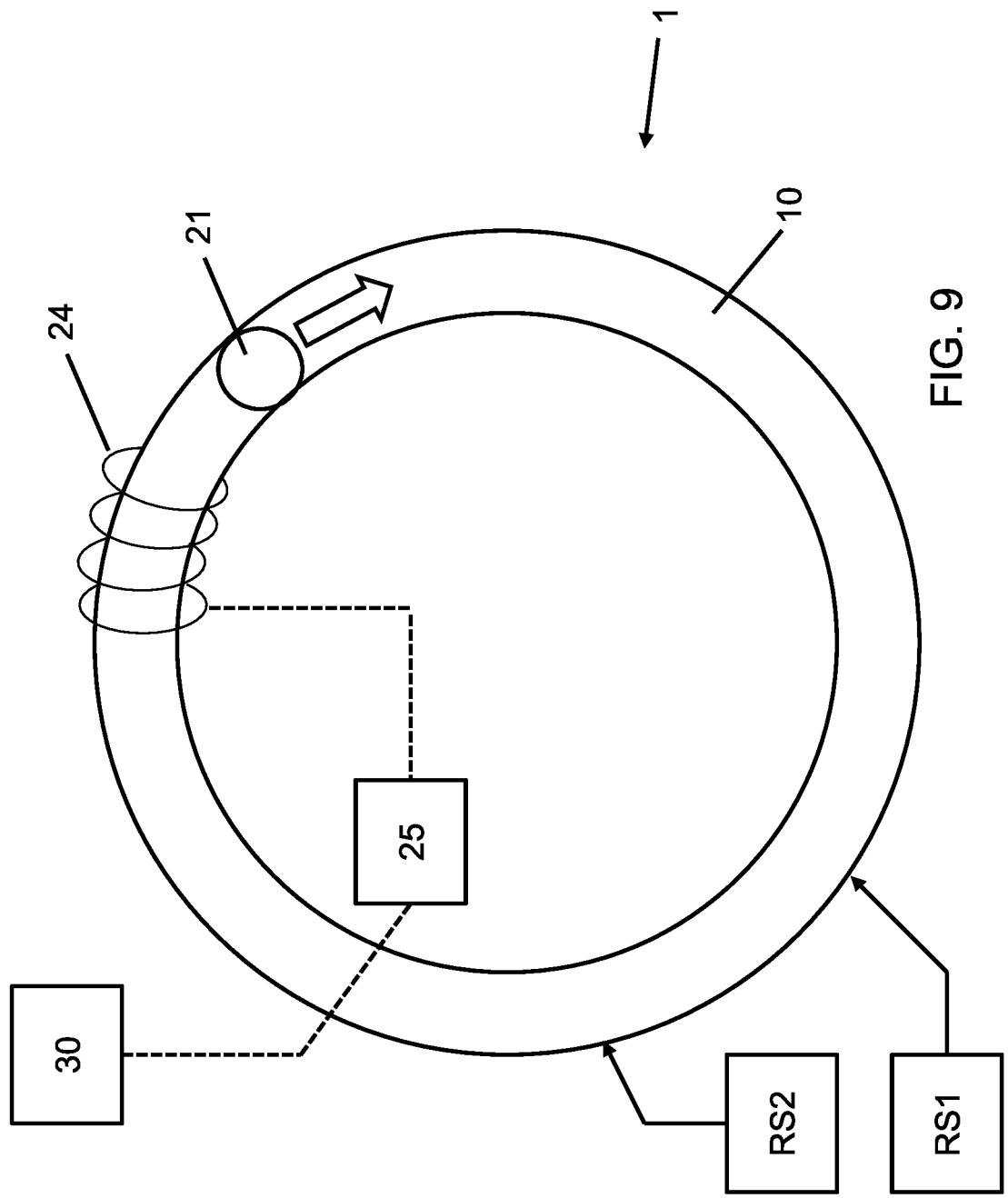
FIG. 9 shows an embodiment that is alternative to the one shown in FIG. 1.

In this embodiment, the displacement device comprises, therefore, the solenoid 24, represented in FIG. 9 as a series of windings, and a control unit 25, appropriately configured to apply the necessary current to the solenoid 24.

The control unit 25 is connected to the processing unit 30, which, as aforesaid, is configured for computing the rheologic parameter of the mud under examination.

Preferably, said rheologic parameter is determined as a function of the magnetic field induced by the applied current intensity.

Preferably, said rheologic parameter comprises a viscosity of the mud.

As an example, the following shows some relations involving B, which is the modulus of the magnetic field induced by the applied current intensity I, based on said geometry.

$$B = \frac{\mu_r \cdot N \cdot I}{2 \cdot \pi \cdot r}$$

Where $\mu_r$ is the magnetic permeability of the medium involved (i.e. the combination of the first toroidal conduit and the mud under examination), N is the number of coils of the solenoid, I is the current intensity through the solenoid, r is the radius from the center of the solenoid (substantially coinciding with the radius of the first toroidal conduit), B is the modulus of the induced magnetic field.

$$B = \frac{F}{I \cdot L}$$

From the modulus of the induced magnetic field, one can obtain the force applied to the projectile as a function of the current intensity and the axial length of the solenoid.

$$F = B \cdot I \cdot L$$

Where L is the axial length of the solenoid. By dividing such force by the area of the internal section of the first toroidal conduit, orthogonal to the projectile's sliding direction, a stress is obtained:

$$\tau_y = \frac{F}{A} \cdot C_D = \frac{\mu_r \cdot N \cdot I^2 \cdot L}{2 \cdot \pi^2 \cdot r \cdot R} \cdot C_D$$
$$\dot{\gamma} = \frac{v}{R}$$
$$\eta = \frac{\tau_y}{\dot{\gamma}}$$

Where $\dot{\gamma}$ is the mean deformation rate profile, v is the mean velocity profile of the mud in the first toroidal conduit, $C_D$ is the coefficient of friction, R is the radius of the cross-section of the first toroidal conduit, η is the mean viscosity profile of the mud under examination.

In one embodiment of the invention, the processing unit 30 and the control unit 25 may be implemented as a single circuit or device; alternatively, they may be implemented as distinct and mutually connected circuits or devices.

Preferably, the first and second operating steps are carried out after the operating conditions have been applied to the mud. In practical terms, this means that, in a preferred embodiment, the mud is first subjected to the operating conditions (computed as described above), and only then the operations for computing the rheologic parameter(s) of the mud are carried out. In this manner, the "history" of the mud, i.e. the set of conditions to which it has been subjected, can adequately affect the computation of the rheologic parameter (s) of the mud, thus ensuring a realistic and reliable evaluation of its on-site performance.

Figure 7:
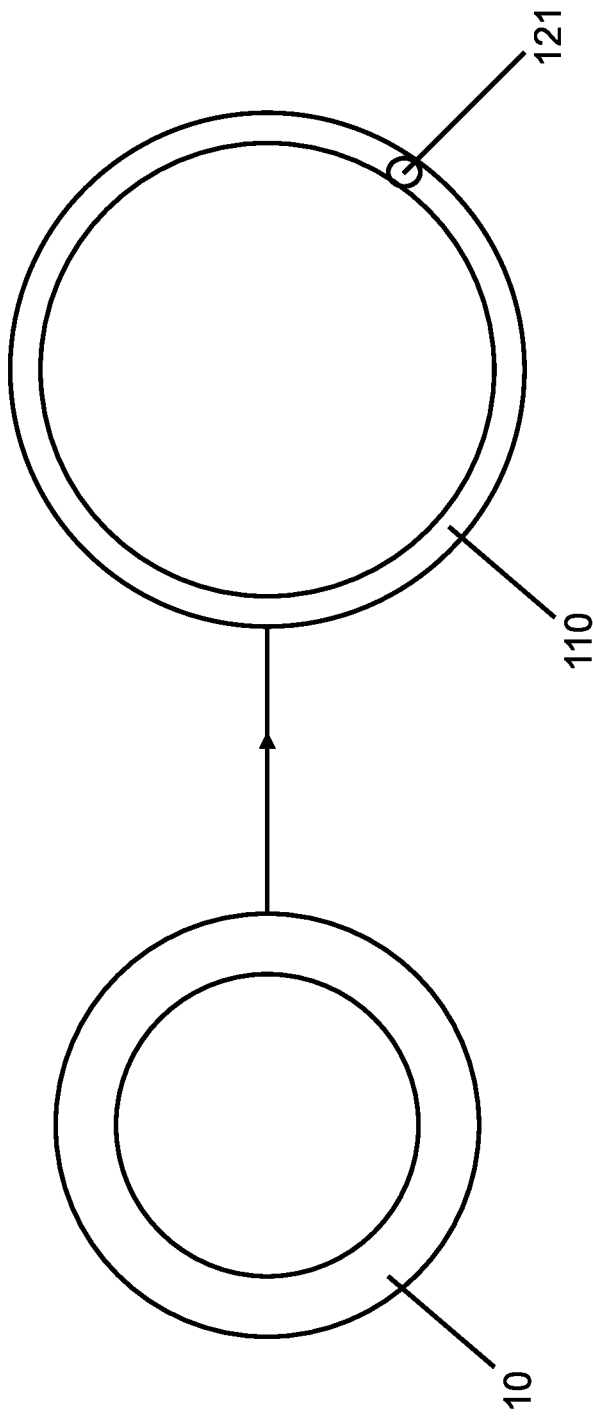
FIG. 7 schematically shows a further embodiment of the apparatus of FIG. 1.

FIG. 7 schematically shows a preferred embodiment of the invention.

Preferably, the apparatus 1 comprises, in addition to the first toroidal conduit 10, also a second closed toroidal conduit 110.

The second toroidal conduit 110 is in selective fluidic communication with the first toroidal conduit 10. This means that, by means of suitable components/devices (e.g. valves), it is possible to keep the two conduits either separate or in fluidic communication, depending on the operating step to be carried out. For example, the mud may be made to flow into the second toroidal conduit 110 after having circulated for a given time interval in the first toroidal conduit 10 (with the second toroidal conduit 110 kept separate).

Preferably, the second toroidal conduit 110 has substantially the same inner volume as the first toroidal conduit 10, but a different diameter and a different cross-sectional area compared with the first toroidal conduit 10.

The second toroidal conduit 110 is associated with respective temperature and pressure regulation systems (not shown), similar to said first and second regulation systems RS1, RS2.

Through the use of the second toroidal conduit 110, and possibly of other additional closed toroidal conduits, all having the same inner volume but different diameter and cross-sectional area, it is possible to simulate in an even more accurate manner the path followed by a drilling mud that, in operation, will flow through successive well segments having different cross-sections and sizes.

Advantageously, the displacement device 20 is configured for moving the mud in the second toroidal conduit 110, so that such mud will flow in the second toroidal conduit 110.

Preferably, the displacement device comprises a second projectile 121, housed inside the second toroidal conduit 110. While it has different dimensions to adapt itself to the different cross-sectional area of the second toroidal conduit 110, the second projectile 121 has substantially the same characteristics as the first projectile 21.

In one embodiment, it is envisaged that the main actuator 23 is also coupled to the second projectile 121. This can be achieved by means of the above-mentioned active element 22 (which will have to be suitably moved when the mud flows from the first toroidal conduit 10 into the second toroidal conduit 110), or by means of a similar active element, driven by the main actuator 23 and magnetically coupled to the second projectile 121.

In one embodiment, the displacement device 20 comprises an auxiliary actuator 123 coupled to the second projectile 121 (through a respective active element) for moving said second projectile 121 inside the second toroidal conduit 110.

It should be noted that, although only the first and second toroidal conduits 10, 110 have been described herein, further toroidal conduits may also be used in order to simulate different path sections in which the mud will have to flow in operation.

In one embodiment, the displacement device 20 comprises a pump (not shown), preferably an electric-type volumetric pump. Such pump acts upon the mud in the first toroidal conduit 10 in order to move the same according to the above-described modalities. The rheologic characteristics of the mud can then be determined as a function of the electric absorption of the pump. Note that said pump may also be used in those configurations which include the second toroidal conduit 110 and other additional toroidal conduits.

Figure 10:
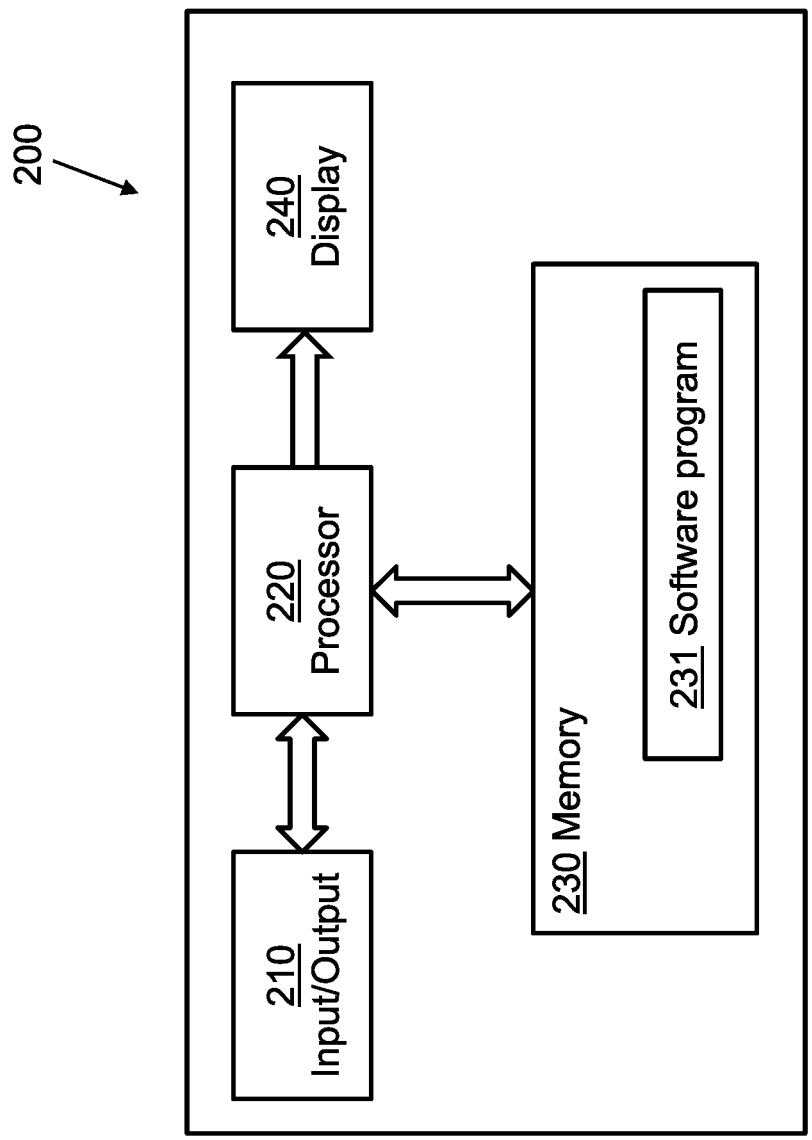
FIG. 10 shows a block diagram of a component of the apparatus according to the present invention.

FIG. 10 shows, by way of example, an electronic device 200, e.g. a computer or a similar apparatus, configured for executing the processing envisaged by the method according to the present invention, by means of which the processing unit 30 can be implemented.

The electronic device 200 is provided with an input/output device 210, which is used for receiving the conditions to be simulated, sending control signals to the displacement device 20, and receiving from the displacement device 20 parameters concerning the operation of the displacement device 20 itself (e.g. parameters related to the torque applied by the main actuator 23 or parameters related to the current applied by the control unit 25). The input/output device 210 can be used for exchanging signals with the first and/or second regulation systems RS1, RS2. The electronic device 200 further comprises a processor 220, which may be implemented as a microprocessor, adapted to execute the processing described and claimed herein. The electronic device 200 may be equipped with a non-volatile memory 230 storing, for example, the geometric parameters of the first toroidal conduit 110 (and of any additional toroidal conduits). The memory 230 may be used for storing a software program 231 comprising instructions that can be read by a computer, i.e. the processor 220, to obtain, as a function of the parameters supplied by the displacement device 20, the rheologic parameter(s) of the drilling mud, as previously described herein. The processor 220 is connected to the input/output device 210 and to the memory 230, and is used for executing the software program in order to obtain rheologic measurements of the drilling mud. The electronic device 200 may comprise a visualization device (reference numeral 240 in FIG. 10), e.g. a display, allowing a user to display the rheologic measurements carried out and possibly also other data generated/processed by the processor 60.

What is claimed is:

1. Method for carrying out rheologic measurements of a drilling mud, comprising:
    providing a first toroidal conduit;
    inserting into said first toroidal conduit a drilling mud, comprising drilling debris;
    determining conditions to be simulated for said mud, said conditions to be simulated comprising a path length and/or a flow time to be simulated for said mud;
    determining, as a function of said conditions to be simulated, operating conditions to be applied to said mud, said operating conditions comprising a number of laps along said first toroidal conduit and/or a flow time in said first toroidal conduit;
    regulating the temperature inside said first toroidal conduit;
    regulating the pressure inside said first toroidal conduit;
    providing a displacement device comprising a first projectile, wherein said first projectile fills substantially entirely a cross-section of said first toroidal conduit;
    moving, by means of said first projectile, said mud in the first annular conduit according to said operating conditions;
    said method further comprising:
    a first operating step, wherein a force is determined, which is applied by said displacement device to move said mud in the first toroidal conduit;
    a second operating step, wherein a rheologic parameter of said mud is determined as a function of said force.

2. Method according to claim 1, wherein said first and second operating steps are carried out at least after said operating conditions have been applied.

3. Method according to claim 1, wherein said force corresponds to a torque that said displacement device applies to keep said mud flowing at a predetermined velocity.

4. Method according to claim 3, wherein said rheologic parameter is determined as a function of said torque.

5. Method according to claim 1, wherein said rheologic parameter comprises a viscosity of said mud.

6. Method according to claim 1, wherein the pressure inside said first toroidal conduit is in the range of 1 bar to 200 bar, preferably 10 bar to 170 bar.

7. Method according to claim 1, wherein the temperature inside said first toroidal conduit is in the range of 4° C. to 200° C., preferably 10° C. to 160° C.

8. Apparatus for carrying out rheologic measurements of a drilling mud comprising drilling debris, said apparatus comprising:
    a first toroidal conduit;
    a first regulation system for regulating the temperature inside said first toroidal conduit;

a second regulation system for regulating the pressure inside said first toroidal conduit;

a displacement device comprising a first projectile, wherein said first projectile fills substantially entirely a cross-section of said first toroidal conduit, said first projectile being configured for moving said drilling mud inside said first toroidal conduit according to operating conditions determined on the basis of conditions to be simulated for said mud, wherein said conditions to be simulated comprise a path length and/or a flow time to be simulated for said mud, and said operating conditions comprise a number of laps along said first toroidal conduit and/or a flow time in said toroidal conduit;

a processing unit, associated with said displacement device and configured for:
  determining a force exerted by said displacement device in order to move the mud in said first toroidal conduit;
  determining a rheologic parameter of said mud as a function of said force.

9. Apparatus according to claim 8, wherein said processing unit is configured for:
  verifying that said operating conditions have been applied;
  after performing said verification, determining the force applied by said displacement device for moving the mud in the first toroidal conduit;
  determining said rheologic parameter as a function of said force.

10. Apparatus according to claim 8, wherein said displacement device comprises:
  an active element, external to said first toroidal conduit and magnetically coupled to said first projectile;
  a main actuator connected to said active element and configured for moving the latter along the first toroidal conduit.

11. Apparatus according to claim 8, wherein said projectile is made of oriented magnetic material, and said displacement device comprises:
  one or more windings arranged around said first toroidal conduit;
  a control unit, connected to said one or more windings and configured to cause a determined current to flow in said one or more windings, said determined current generating a magnetic field adapted to move said first projectile.

12. Apparatus according to claim 11, wherein said control unit is connected to said processing unit, said processing unit being configured to determine said rheologic parameter as a function of the applied current.

13. Apparatus according to claim 8, wherein said first regulation system comprises at least one of:
  a sleeve externally associated with said first annular conduit, a thermovector fluid and a regulation module for regulating the temperature of said thermovector fluid, and
  one or more Peltier cells externally applied to said first toroidal conduit, and an electric circuit associated with said one or more Peltier cells in order to supply power thereto.

14. Apparatus according to claim 8, wherein said first toroidal conduit has an aperture, which can be selectively closed, for inserting said mud into said first toroidal conduit.

15. Apparatus according to claim 14, comprising a closing element coupled to said aperture and drivable between a first condition, in which it sealingly closes said aperture, and a condition in which it opens, at least partially, said aperture.

16. Apparatus according to claim 8, comprising a second toroidal conduit, in selective fluidic communication with said first toroidal conduit, wherein said second toroidal conduit has substantially the same inner volume as said first toroidal conduit, and a different diameter and cross-sectional area compared to said first toroidal conduit.

17. Apparatus according to claim 16, wherein said displacement device is configured for moving said mud in said second toroidal conduit, so that said mud will flow in said second toroidal conduit.

18. Apparatus according to claim 16, wherein said displacement device comprises a second projectile housed inside said second toroidal conduit.

19. Apparatus according to claim 18, wherein said main actuator is also coupled to said second projectile.

20. Apparatus according to claim 18, wherein said displacement device comprises an auxiliary actuator coupled to said second projectile for moving said second projectile inside said second toroidal conduit.

21. Apparatus according to claim 10, wherein said displacement device comprises a pump, preferably an electric-type volumetric pump, adapted to act upon said mud in order to move the same at least inside said first toroidal conduit.

* * * * *

UNITED STATES PATENT AND TRADEMARK OFFICE
CERTIFICATE OF CORRECTION

| | |
|---|---|
| PATENT NO. | : 11,441,989 B1 |
| APPLICATION NO. | : 17/679157 |
| DATED | : September 13, 2022 |
| INVENTOR(S) | : Antonio Calleri |

It is certified that error appears in the above-identified patent and that said Letters Patent is hereby corrected as shown below:

On the Title Page

Item [73] "San Glullano Milanese" should be changed to -- San Giuliano Milanese --

Item [22] "Feb. 24, 2020" should be changed to -- Feb. 24, 2022 --

Signed and Sealed this
Fourteenth Day of February, 2023

Katherine Kelly Vidal
*Director of the United States Patent and Trademark Office*